United States Patent [19]

Gabby et al.

[11] 4,046,874

[45] Sept. 6, 1977

[54] SOAPLESS SHAVE COMPOSITION

[75] Inventors: John Lester Gabby; Dennis Dale Corbin; Jack Bruner Lowe, all of Evansville, Ind.

[73] Assignee: Mead Johnson & Company, Evansville, Ind.

[21] Appl. No.: 632,427

[22] Filed: Nov. 17, 1975

Related U.S. Application Data

[60] Division of Ser. No. 442,015, Feb. 13, 1974, Pat. No. 3,936,391, which is a division of Ser. No. 153,837, June 16, 1971, Pat. No. 3,809,764, which is a continuation-in-part of Ser. No. 74,211, Sept. 21, 1970, abandoned.

[51] Int. Cl.$^2$ .............................................. A61K 7/15
[52] U.S. Cl. ........................................ 424/73; 424/47; 424/357; 426/116; 426/664
[58] Field of Search ............................ 424/73, 357, 47

[56] References Cited

U.S. PATENT DOCUMENTS

| 2,192,907 | 3/1940 | Harris | 424/73 X |
| 2,366,759 | 1/1945 | Thomas et al. | 424/73 |
| 2,548,891 | 4/1951 | Gantner | 424/DIG. 5 |

FOREIGN PATENT DOCUMENTS

| 1,248,192 | 10/1960 | France | 424/73 |
| 1,147,712 | 4/1963 | Germany | 424/73 |

*Primary Examiner*—Dale R. Ore
*Attorney, Agent, or Firm*—R. E. Carnahan; R. H. Uloth

[57] ABSTRACT

A unique shaving cream containing no soap, fat or oil which functions without pre-wetting the skin is formed from an aqueous foam containing 0.5 to 7.5% by weight of a polyglycerol ester and from 2 to 10% by weight of a water insoluble pulverulent bodying agent to provide the desired texture.

2 Claims, No Drawings

4,046,874

SOAPLESS SHAVE COMPOSITION

CROSS REFERENCE TO RELATED APPLICATIONS

This application is a divisional of U.S. patent application Ser. No. 442,015 filed Feb. 13, 1974 and now U.S. Pat. No. 3,936,931 patented Feb. 3, 1976 which in turn is a divisional of U.S. patent application Ser. No. 153,837 filed June 16, 1971 and now U.S. Pat. No. 3,809,764, patented May 7, 1974. The latter is a continuation-in-part of U.S. application Ser. No. 74,211 filed Sept. 21, 1970 and now abandoned.

FIELD OF THE INVENTION

This invention involves a shaving preparation which contains substantially no soap, fat, or oil and functions without wetting the skin to be shaved prior to application of the preparation thereto. It is comprised of an aqueous foam containing a polyglycerol ester as foaming agent and includes a water insoluble pulverulent bodying agent to confer the desired texture upon the preparation.

BACKGROUND OF THE INVENTION

Within the last 10 years a large body of art has developed involving the formulation of dietary products for weight control purposes particularly for consumption by obese individuals. Development has taken two directions. One has involved the formulation of dietary products providing in themselves complete nutrition so that an obese individual could substitute a measured quantity of such products for his normal food. In this way convenient and accurate control of caloric intake was possible, and yet adequate nutrition was maintained with respect to protein, fat, carbohydrate, vitamin, and mineral intake.

Other developments have not involved nutrition as such, but rather the preparation of imitation foods having very low caloric value yet closely resemble conventional food products. Such products are attractive for weight control diets and other special diets for the restriction of fats, carbohydrate, salt, residue, etc. since they may be ingested in substantially unlimited quantities and are useful for consumption when eating as a social activity rather than one simply to maintain life. They provide the gustatory pleasure of consuming various types of foods which would otherwise be unavailable or restricted because of the requirements of the special diet. The present invention involves compositions of this latter type.

The compositions of the present invention may be classified as imitation butter, margarine, cheese spreads, dips, frozen desserts including ice cream and sherbert, puddings, icings, salad dressings, sauces, and the like. They depend largely for their character on the polyglycerol fatty esters as emulsifiers or foaming agents. The latter substances are accepted as food additives under Title 21, Code of Federal Regulations, Section 121.1120. They have been known for many years having been first described in the chemical literature as early as 1930. Improved polyglycerol fatty esters are described in Belgian Pat. No. 623,179 published Apr. 4, 1963 (Chemical Abstracts 60, 13803b). The polyglycerol esters have been widely used in margarine manufacture as anti-spattering ingredients and in the preparation of shortening compositions for use in the preparation of confections and pastries because of their emulsifying qualities. Refer for example to U.S. Pat. No. 3,230,909 and Belgian Pat. No. 656,949 dated June 10, 1965 (Chemical Abstracts 65, 6204d).

SUMMARY OF THE INVENTION

The compositions of the present invention are aqueous foams of various densities containing up to 55% by weight of non-aqueous ingredients in the liquid phase and containing as emulsifier or foaming agent from 0.33 to 7.5% by weight of a polyglycerol fatty ester and as stabilizer for the emulsion from 0.2 to 3% by weight of a hydrophilic colloid. The products preferably contain additional ingredients such as flavoring, coloring, dispersing and bodying ingredients as may be required to provide the desired physical and organoleptic qualities. For example, in the preparation of a product resembling whipped cream small amounts of sugar or artificial sweetener, cream flavor and in some instances vanilla flavor are included. In any event, such supplementary ingredients are present in such amount that the total composition of the aqueous phase contains no more than 55% by weight of non-aqueous ingredients.

Suitable products can be prepared employing as little as from 0.33 to 2% of polyglycerol fatty ester as emulsifier but the resesulting foams are rather grainy, large-celled, and unstable when whipped to maximum expansion. When whipped to less than maximum expansion, satisfactory texture can be obtained. For products where maximum expansion on whipping is used, it is preferred to use at least about 2% by weight of polyglycerol fatty ester and higher concentrations up to about 7.5% depending upon the the desired texture or fat-like quality to be achieved. If approximately 5% by weight of polyglycerol fatty ester is employed a spread resembling whipped butter or a cheese spread is obtained. With a lesser amount of polyglycerol fatty ester, for example about 3%, the oleaginous character diminishes and a lighter product resembling whipped cream is obtained. The preferred polyglycerol ester concentration range for spreads and whipped toppings is 2% to 5% by weight. For frozen desserts such as imitation ice cream, ice milk, or sherbert where a much lower degree of expansion is desired, e.g. 50 – 110% (0.50 to 1.1 fold), from 0.5 to 1.0% by weight of emulsifier is preferred and the degree of expansion is controlled by the amount of whipping or mixing.

The foregoing spreads and whipped toppings are stable only for a short period unless a hydrophilic colloid is included in the composition as stabilizer. Suitable hydrophilic colloids include the vegetable gums such as acacia gum, xanthan gum, or other well known gums such as locust bean gum and carrageenan. Other hydrophilic colloids that are suitable are water soluble proteins such as gelatin, and water dispersible polysaccharides such as pectin, carboxy-methylcellulose, starch (preferably pregelatinized), etc. The simple disaccharides or trisaccharides such as sucrose which form true solutions are not considered hydrophilic colloids for present purposes.

The hydrophilic colloid ingredient is used in an amount ranging from 0.2 to 3% by weight of the aqueous phase. In addition to acting as stabilizers they also improve the texture of the final whipped product. For instance, with imitation ice creams the stabilizer also serves the function of delaying or preventing undesired crystallization of ice or sugars, etc. For these products the amount of stabilizer is limited to about 0.2 to 0.5% by weight to avoid so-called "melt resistance". For ice cream, a liquid melt is desired and excess stabilizer prevents this with formation of a stiff, pudding-like melt. A more complete list of suitable hydrophilic colloids is published in "Handbook of Food Additives", Chemical Rubber Publishing Company, Cleveland, Ohio, 1968, page 315.

The most preferred polyglycerol ester for use in the present invention is triglycerol monostearate. Other polyglycerol esters having from 3 to 10 glycerol units in the polyglycerol chain and 1 or 2 saturated fatty ester groups are, however, operable. The preferred fatty esters are the stearate esters but the palmitate and arachidic esters are also operable. The latter fatty acyl groups contain respectively 16 to 20 carbon atoms. A suitable polyglycerol monostearate (chiefly the triglycerol product) for use in this invention is Durkreme 310 of the Durkee Division of S.C.M. Company. Other useful polyglycerol esters are Drewpol 6-2-S and Drewpol 12-2-S of Drew Chemical Corporation. These are respectively hexaglycerol distearate and decaglycerol distearate.

Polyglycerol fatty esters are wax-like solids which are rather inconvenient to handle in manufacturing operations. They may be melted and blended with some of the other ingredients at a temperature of about 160° F. or higher. We have found it convenient to convert the waxy polyglycerol fatty esters into a finely comminuted condition which makes possible dry blending thereof with other ingredients. One means used to accomplish this is by melting the polyglycerol fatty ester and then passing the molten ester through a spray dryer operated with cold air (30° C. or less) as cooling medium. This results in conversion of the molten material into a fine spray and solidification of the individual droplets to provide a discrete particulate solid. Sometimes other ingredients are mixed or suspended in the molten emulsifier prior to spray cooling. The particulate nature and foaming qualities are unaffected by incorporation of up to 10% by weight of water. Lecithin, may be incorporated at this point to improve the texture of the final foam product. If an anti-caking ingredient is used such as sodium silicoaluminate, up to 12% may be incorporated before spray cooling.

Preparation of the whipped toppings or spreads involves rapidly agitating or whipping the polyglycerol fatty ester with the amount of water selected for the particular batch at a temperature in the range of 125° F. to 212° F. The object of heating within this temperature range is to hydrate and disperse the polyglycerol ester. It has been found that hydration takes place within a rather narrow temperature range of about 125°-135° F. Whipping of the mixture should take place in a mechanical device designed for mixing the air therewith and creating a foam. A suitable device is a household electric mixer operated at relatively high speed and for a sufficient period to produce a foam which does not expand upon further whipping. In practive, all ingredients except the vegetable gum stabilizer are agitated with hot water in the foregoing fashion. Dispersion of the polyglycerol ester thus takes place, but actual hydration thereof is believed to occur as the mixture cools through the temperature range of 125°-135° F.

When a vegetable gum is used as stabilizer it is preferably added as a second stage after full foam development, and mixing is continued just sufficiently to effect dispersion thereof throughout the mixture. Two stage addition of ingredients in this fashion is recommended since the vegetable gums rapidly hydrate and prevent the proper degree of air emulsification when using a simple mechanical mixer if included at the outset. A one stage process according to which all ingredients are incorporated at the outset is, however, operable when using a protein or polysaccharide stabilizer since rapid hydration with the attendant increase in viscosity does not occur with the hydrocolloids other than the vegetable gums.

The resulting product is bland and substantially tasteless although it has the appearance and texture of whipped cream or an oleaginous spread depending upon the concentration of polyglycerol fatty ester employed. In order to mimic conventional food products of the intended types, flavoring, bodying, and coloring agents are employed. For example, imitation butter can be prepared by simply adding a small amount of butter flavor and color and sufficient salt to give the appropriate taste to the foregoing emulsion to obtain a product very closely resembling whipped butter.

For the preparation of products resembling whipped toppings or desserts, a bodying ingredient is sometimes employed to provide the appropriate texture. Either nutritive or non-nutritive materials can be used for this purpose. Dextran is an example of a non-nutritive material that is quite suitable. Sugar is preferred for lending body and texture to a whipped cream-like product. For the preparation of a chocolate dessert cocoa is employed. For imitation ice cream, non-fat milk solids and sugar are employed. This aspect of the invention is subject to almost infinite variation and selection of appropriate ingredients and combinations are at the choice of the skilled operator. In any event, the total amount of bodying ingredients employed does not exceed 45% by weight of the composition. Suitable bodying ingredients in addition to those mentioned above are fructose, dried egg white, and insulin.

A unique feature of the present compositions is that they are oleaginous in appearance and texture, but contain substantially no fat. Small amounts of fat may, however, be inherently included because of its presence in certain of the ingredients. For example, when cocoa is used as a flavoring and bodying ingredient a small amount of fat is inherently present because it is contained in the coaoa. Again, in the preparation of an imitation cheese dip or peanut butter the natural materials which contain a certain amount of fat are needed for flavoring since artificial cheese and peanut butter flavors are not available. In any event, the amount of fat in the final product does not exceed 5% by weight thereof thus making possible the preparation of low calorie products.

Another means for varying the caloric content is by regulation of the degree of expansion on whipping since the size of a serving portion is ordinarily determined by volume. Each of the compositions of the present invention undergoes a specific amount of expansion on whipping in the air which is related to its composition including the content of polyglycerol ester emulsifier. Generally speaking, the lower the concentration of polyglycerol ester employed the greater the maximum degree of expansion. For example, at the 2 to 3% level a foam resembling whipped cream is obtained in which the amount of expansion is approximately 5 to 6 fold relative to the aqueous solution prior to whipping. At the 5% level of polyglycerol ester a lower degree of expansion of about two folds occurs resulting in a more oleaginous appearing product such as a spread. Futher modification of the degree of expansion and thus the density of the final whipped product can be effected by adding a fat or fatty material. This reduces expansion and increases density.

For the frozen desserts such as imitation ice creams where the amount of polyglycerol ester is restricted to the range of 0.5 to 1.0% to balance the requirements of stability and mouth feel, maximum whipping is not employed. Here mixing is continued to an "over run" of 50 to 110% i.e. 0.5 to 1.1 fold expansion.

DESCRIPTION OF SPECIFIC EMBODIMENTS

I. Aerosol Toppings and Spreads

The foregoing disclosure has been directed primarily to the preparation of toppings and spreads extemporaneously in the kitchen or home. The following example involves a modification of the blending and whipping steps as described above which can be carried out in industrial equipment to provide a liquid concentrate suitable for delivery from an aerosol container using either nitrous oxide alone or in combination with one of the low-boiling fluorinated hydrocarbons approved for use in aerosol packaging of food products. This modification involves dispersing or dissolving all of the ingredients in the full amount of water to be used in the final product, but accomplishing the dispersion in such a way as to avoid incorporating air and thus obtaining a foam or an air-in-water emulsion as described above. This is accomplished by using a mechanical homogenizer which mixes the ingredients in a closed system and thus avoids the formation of the foam. A foam is subsequently formed on delivery of the composition from the valve of the aerosol container. The following example illustrates this.

EXAMPLE A

Imitation Butter for Aerosol Delivery

The following ingredients are mixed with heating to about 170° F. in a closed vessel having no free air space above the liquid. The blend is then fed to a mechanical homogenizer and the resulting homogenized liquid is used as the liquid phase for an aerosol container.

Water 170.0 g.
Triglycerol Monostearate 8.0 g.
Sodium Silicoaluminate 0.2 g.
Gum Acacia 5.0 g.
Xanthan Gum 1.0 g.
Salt 3.5 g.
Butter Flavor and Color 0.54 g.

When the foregoing is expelled through the valve of a conventional aerosol container the extruded product forms a foam or emulsion which has the consistency of whipped butter and insofar as organoleptic character is concerned, it is substantially identical with whipped butter.

II. Shaving Cream

It has been noted that a shaving foam can be prepared by hydration of a polyglycerol ester and whipping with water as has been described above for the various food products. From 2 – 10% by weight of a water insoluble pulverulent bodying agent such as dextran, cellulose, talc, silica, sodium silicoaluminate, Fuller's earth, clay, etc. is included to provide the appropriate texture to the foam. The hydrophilic colloid foam stabilizer is not required for this product. Suitable perfumes, etc. are included for elegance. A microbiological preservative is used to improve storage stability. This is a highly unique shaving cream since it contains no soap, fat or oil and functions without additional water. Its lubricating action makes possible an extremely close shave and the residue may be whipped off or washed away. It leaves the skin with the feeling of having been treated with cold cream. Example B which follows illustrates the preparation of such a shaving cream.

EXAMPLE B

Shaving Cream

Step A. Glycerol 5.5 g., triglycerol monostearate 5.5 g., and water 5.5 g. is formed into a homogeneous cream-like paste by warming at 135° F. The mixture is then allowed to cool and mixed with 68.3 g. of water, 2.8 g. of sodium silicoaluminate, 1.4 g. of 5% solution of menthol in alcohol, and 0.03 g. of a preservative consisting of 1 part propylparabens and 4 parts methylparabens (weight basis). The resulting product is used as the liquid fill for an aerosol dispenser. It may also be dispensed in a jar or tube. It is preferred that it be applied to the face or other surface to be shaved without mixing with additional water and with the surface dry.

What is claimed is:

1. A shaving cream adapted for dry shaving with a conventional razor blade which comprises an aqueous foam containing in the aqueous pahse from 0.5 to 7.5% by weight of a polyglycerol ester molecularly constituted of from 3 to 10 glycerol units and from 1 to 2 fatty acyl ester groups each containing from 16 to 20 carbon atoms and a texturizing amount of from 2 to 10% by weight of a water insoluble pulverulent bodying agent, wherein said composition contains substantially no soap, fat, or oil.

2. The shaving cream of claim 1 wherein said pulverulent bodying agent is selected from the group consisting of dextran, cellulose, talc, silica, sodium silicoaluminate, and clay.

* * * * *